(12) United States Patent
Blank et al.

(10) Patent No.: US 10,687,710 B2
(45) Date of Patent: Jun. 23, 2020

(54) DEVICE AND METHOD FOR PALPATION OF TISSUES FOR CHARACTERIZATION AND MECHANICAL DIFFERENTIATION OF SUBCUTANEOUS STRUCTURES

(71) Applicant: Carnegie Mellon University, Pittsburgh, PA (US)

(72) Inventors: Molly Blank, Pittsburgh, PA (US); James Antaki, Pittsburgh, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 695 days.

(21) Appl. No.: 15/318,703

(22) PCT Filed: Jun. 16, 2015

(86) PCT No.: PCT/US2015/036008
§ 371 (c)(1),
(2) Date: Dec. 14, 2016

(87) PCT Pub. No.: WO2015/195649
PCT Pub. Date: Dec. 23, 2015

(65) Prior Publication Data
US 2017/0143208 A1    May 25, 2017

Related U.S. Application Data

(60) Provisional application No. 61/998,030, filed on Jun. 16, 2014.

(51) Int. Cl.
*A61B 5/00* (2006.01)
(52) U.S. Cl.
CPC .......... *A61B 5/0053* (2013.01); *A61B 5/0077* (2013.01); *A61B 5/4312* (2013.01); *A61B 5/6885* (2013.01); *A61B 5/6886* (2013.01)

(58) Field of Classification Search
CPC .... A61B 5/0048; A61B 5/0051; A61B 5/0053
See application file for complete search history.

(56) References Cited

U.S. PATENT DOCUMENTS 5,833,633 A * 11/1998 Sarvazyan ........... A61B 1/0052
600/587
2001/0031934 A1   10/2001 Sarvazyan et al.
(Continued)

FOREIGN PATENT DOCUMENTS

WO         9938440 A1    8/1999
WO      2011076886 A2    6/2011

OTHER PUBLICATIONS

Ayyildiz et al., "A Novel Tactile Sensor for Detecting Lumps in Breast Tissue," 2010, p. 367-372.
(Continued)

*Primary Examiner* — Allen Porter
(74) *Attorney, Agent, or Firm* — The Webb Law Firm

(57) ABSTRACT

A palpation device for palpation of tissues for characterization (e.g., qualification and/or quantification) of subcutaneous structures is provided. The palpation device includes a frame formed from a substantially rigid material and comprising an opening; a tonometric lens extending through the opening of the frame; and a radiation source. The lens is configured to at least partially impinge a tissue of interest to identify an object embedded therein. The lens includes a body having a reflective coating on an outer surface thereof. The radiation source is positioned to illuminate the reflective coating such that a topography of the coating can be observed. The body includes a body material that is as stiff or stiffer than the tissue of interest and less stiff than the embedded object to be characterized. A system including the palpation device and an image device for obtaining an image through the lens is also provided.

29 Claims, 16 Drawing Sheets

(56) References Cited

U.S. PATENT DOCUMENTS

2010/0087756 A1     4/2010    Egorov et al.
2010/0179429 A1     7/2010    Ho et al.

OTHER PUBLICATIONS

Barlow et al., "Accuracy of Screening Mammography Interpretation by Characteristics of Radiologists," J. Natl. Cancer Inst., 2004, p. 1840-1850, vol. 96:24.

Bleyer et al., "Effect of Three Decades of Screening Mammography on Breast-Cancer Incidence," N. Engl. J. Med., 2012, p. 1998-2005, vol. 367:21.

Campbell et al., "The Costs of Treating Breast Cancer in the US: A Synthesis of Published Evidence," Pharmacoeconomics, 2009, p. 199-209, vol. 27:3.

Egorov et al., "Differentation of Benign and Malignant Breast Lesions by Mechanical Imaging," Breast Cancer Res. Treat., 2009, p. 67-80, vol. 118:1.

Gotzche et al., "Screening for Breast Cancer with Mammography (Review)," Cochrane Database of Systematic Reviews, 2013, p. 1-81, No. 6.

Howlader et al., "SEER Cancer Statistics Review, 1975-2009 (Vintage 2009 Populations)," Bethesda, MD, 2012 p. 1-107.

Kardinah et al., "Short Report: Limited Effectiveness of Screening Mammography in Addition to Clinical Breast Examination by Trained Nurse Midwives in Rural Jakarta, Indonesia," Int. J. Cancer, 2014, p. 1250-1255, vol. 134:5.

Kovesi, "Phase Congruency Detects Corners and Edges," 2003, p. 309-318.

Liu, "Beyond Pixels: Exploring New Representations and Applications for Motion Analysis," Massachusetts Institute of Technology, 2009, p. 1-164.

Mathis et al., "Palpable Presentation of Breast Cancer Persists in the Era of Screening Mammography," J. Am. Coll. Surg., 2010, p. 314-318, vol. 210:3.

Miller et al., "Twenty Five Year Follow-Up for Breast Cancer Incidence and Mortality of the Canadian National Breast Screening Study: Randomised Screening Trial," BMJ, 2014, p. 348-366, vol. 348:119.

Nass et al., "Mammography and Beyond: Developing Technologies for the Early Detection of Breast Cancer." 2001, p. 1-312.

O'Donoghue et al., "Aggregate Cost of Mammography Screening in the United States: Comparison of Current Practice and Advocated Guidelines," Ann Intern. Med., 2014, vol. 160:3, p. 145-154.

Pace et al., "A Systematic Assessment of Benefits and Risks to Guide Breast Cancer Screening Decisions," JAMA, 2014, p. 1327-1335, vol. 311: 13.

Pijpe et al., "Exposure to Diagnostic Radiation and Risk of Breast Cancer Among Carriers of BRCA 1/2 Mutations: Retrospective Cohort Study (GENE-RAD-RISK)," BMJ, 2012, p. 1-15, vol. 345.

Ries et al., "Cancer Survival Among Adults: U.S. SEER Program, 1988-2001, Patient and Tumor Characteristics," National Cancer Institute, SEER Program, NIH, 2007 p. 1-276.

Rosolowich et al., "Breast Self-Examination," J. Obstet. Gynaecol Can, 2006, p. 728-730, vol. 28:8.

Sarvazyan et al., "Tactile Sensing and Tactile Imaging in Detection of Cancer," Biosensors and Molecular Technologies for Cancer Diagnostics, 2011, p. 339-354.

Xu et al., "Breast Tumor Detection Using Piezoelectric Fingers: First Clinical Report," J. Am. Coll. Surg., 2013, p. 1168-1173, vol. 216:6.

\* cited by examiner

DEVICE AND METHOD FOR PALPATION OF TISSUES FOR CHARACTERIZATION AND MECHANICAL DIFFERENTIATION OF SUBCUTANEOUS STRUCTURES

CROSS REFERENCE TO RELATED APPLICATIONS

The present application is a national stage of International Patent Application No. PCT/US2015/036008, filed Jun. 16, 2015, which claims the benefit of U.S. Provisional Application Ser. No. 61/998,030, filed Jun. 16, 2014, the entire disclosure of each of which is hereby incorporated by reference in its entirety.

STATEMENT REGARDING FEDERALLY SPONSORED RESEARCH

This invention was made with government support under Grant No. EB003392 awarded by the National Institutes of Health. The government has certain rights in the invention.

BACKGROUND

Technical Field

The present disclosure relates to devices and methods for palpation of tissues for characterization (e.g., qualification and/or quantification) of subcutaneous structures and, in particular, to a device and method including a tonometric lens configured to impinge upon tissues of interest for visualization and/or characterization of subcutaneous structures therein.

Background

Based on current incidence rates, 12.4% (e.g., one out of every eight women born in the United States today) will develop breast cancer at some time during her life. N. Howlader, A. Noone, and M. Krapcho, "SEER Cancer Statistics Review, 1975-2009," Bethesda, Md., 2012. Despite advances in imaging technologies and clinical practice, breast cancer screening has shown a minimal and inconsistent impact in decreasing breast cancer-associated deaths while accumulating nearly $8 billion in associated annual costs. Specifically, the American Cancer Society estimates that 232,340 women were affected in 2013 by first diagnoses of breast cancer. For each woman, the estimated cost of treatment ranges from $20,000 to $100,000 with annual economic burden of breast cancer in the United States upwards of $20 billion. J. D. Campbell and S. D. Ramsey, "The costs of treating breast cancer in the US: a synthesis of published evidence," *Pharmacoeconomics*, vol. 27, no. 3, pp. 199-209, January 2009. The earlier the breast cancer is detected, the better the clinical outcome and the lower the cost. L. Ries, J. J. Young, G. Keel, M. Eisner, Y. Lin, and M.-J. Horner, "Cancer Survival Among Adults: US SEER Program, 1988-2001," *Patient Tumor Charact. Natl. Cancer Institute, SEER Program, NIH*, no. 07, 2007. In an effort to diagnose early stages of the disease, more than $7.8 billion of the spending was attributable to screening practices in 2010. C. O'Donoghue and M. Eklund, "Aggregate cost of mammography screening in the United States: comparison of current practice and advocated guidelines," *Ann. Intern. Med.*, pp. 145-154, 2014. Although screening has increased the incidence of early-stage cancers detected, one study showed only 8 of 122 early stage cancers diagnosed would have progressed to an advanced stage of the disease, a mere 7%. The same study estimates that as many as one third of all patients treated for breast cancer may be over-diagnosed. A. Bleyer and H. G. Welch, "Effect of three decades of screening mammography on breast-cancer incidence," *N. Engl. J. Med.*, vol. 367, no. 21, pp. 1998-2005, November 2012.

The two most common methods of population-wide screening are mammographic imaging and breast self-examination (BSE). As tissues become more cancerous and diseased, cells become necrotic to become denser and stiffer. Measured sensitivity and specificity values vary significantly with breast density, skill and experience of the radiologist and the quality of equipment used. W. E. Barlow, C. Chi, P. a Carney, S. H. Taplin, C. D'Orsi, G. Cutter, R. E. Hendrick, and J. G. Elmore, "Accuracy of screening mammography interpretation by characteristics of radiologists," *J. Natl. Cancer Inst.*, vol. 96, no. 24, pp. 1840-50, December 2004. Risks of screening include those associated with radiation exposure, psychological stress from false positive findings, and any harms from unnecessary treatment. See, e.g., P. Gøtzsche and M. Nielsen, "Screening for breast cancer with mammography," *Cochrane Database Syst Rev*, no. 6, 2009, and L. Pace and N. Keating, "A Systematic Assessment of Benefits and Risks to Guide Breast Cancer Screening Decisions," *JAMA*, vol. 311, no. 13, pp. 1327-1335, 2014. There is even indication that women genetically predisposed to breast cancer with the BRCA1/2 mutation are twice as likely to develop cancer in response to radiographic screening if exposed before the age of 30. A. Pijpe, N. Andrieu, D. F. Easton, A. Kesminiene, E. Cardis, S. Peock, P. Manders, I. Thierry-chef, M. Hauptmann, D. Goldgar, M. A. Rookus, and F. E. Van Leeuwen, "Exposure to diagnostic radiation and risk of breast cancer among carriers of BRCA1/2 mutations: retrospective cohort study (GENE-RAD-RISK)," vol. 345, no. October, p. 2012, 2012. BSE intuitively utilizes the increased stiffness of the lesion by using tactile feedback to feel for "lumps." Although BSE is advocated as an affordable method of screening, it is also associated higher biopsy rates, an increased chance of referral to mammography, and patient stress. V. Rosolowich, R. Lea, P. Levesque, F. Weisberg, J. Graham, and L. McLeod, "SOGC COMMITTEE OPINION: Breast Self-Examination," *J Obs. Gynaecol*, vol. 28, no. 181, pp. 728-730, 2006. Further, because women are generally reluctant to self-refer for mammography, the primary care physician (PCP) is the primary gateway to screening. S. Nass, I. Henderson, and J. Lashof, *Mammography and beyond: developing technologies for the early detection of breast cancer.* 2001, p. 312. However, the PCP must rely on physical examination to make the determination that a patient may be developing a cancerous lesion. Without any quantitative evidence, he/she must convince the patient based on his/her qualitative assessment of a palpable mass. No method is currently used to aid clinical inspections to quantify the shape and mechanical characteristics of the interrogated tissue, rendering it an inherently qualitative test.

Although many professionals continue to advocate for one or both screening practices, clinical trials evaluating mammography and BSE have found increased incidence of early-stage cancers detected, yet results vary from a 19% reduction in mortality to no significant effect on survival rates. See, A. Pijpe, N. Andrieu, D. F. Easton, A. Kesminiene, E. Cardis, S. Peock, P. Manders, I. Thierry-chef, M. Hauptmann, D. Goldgar, M. A. Rookus, and F. E. Van Leeuwen, "Exposure to diagnostic radiation and risk of breast cancer among carriers of BRCA1/2 mutations: retrospective cohort study (GENE-RAD-RISK)," vol. 345, no. October, p. 2012, 2012; a.B. Miller, C. Wall, C. J. Baines, P. Sun, T. To, and S. a. Narod, "Twenty five year follow-up for breast cancer incidence and mortality of the Canadian National Breast Screening Study: randomised screening trial," *Bmj*, vol. 348, no. February 11 9, pp. g366-g366, February 2014; and S. VF, M. AG, M. VM, P. SA, K. RS, S. IK, P. RT, M. NSh, O. AA, B. NIu, I. OA, and I. VG, "Results of a prospective randomized investigation [Russia (St. Petersburg)/WHO] to evaluate the significance of self-examination for the early detection of breast cancer," *Vopr Onkol.*, vol. 49, no. 4, pp. 434-41, 2003. Even despite mammographic screening practices, 43% of identified cancers continue to present as symptomatic, including palpable masses. K. L. Mathis, T. L. Hoskin, J. C. Boughey, B. S. Crownhart, K. R. Brandt, C. M. Vachon, C. S. Grant, and A. C. Degnim, "Palpable presentation of breast cancer persists in the era of screening mammography," *J. Am. Coll. Surg.*, vol. 210, no. 3, pp. 314-8, March 2010. In light of the mixed results for population-wide screening, the question remains: how to improve clinical outcomes from screening while preventing needless tests or treatment and minimizing the associated harms? A growing consensus acknowledges the importance of BSE and mammography, but calls for alternative and complimentary decision-making tools to help guide patients and their physicians. See, J. D. Campbell and S. D. Ramsey, "The costs of treating breast cancer in the US: a synthesis of published evidence," *Pharmacoeconomics*, vol. 27, no. 3, pp. 199-209, January 2009; A. Pijpe, N. Andrieu, D. F. Easton, A. Kesminiene, E. Cardis, S. Peock, P. Manders, I. Thierry-chef, M. Hauptmann, D. Goldgar, M. A. Rookus, and F. E. Van Leeuwen, "Exposure to diagnostic radiation and risk of breast cancer among carriers of BRCA1/2 mutations: retrospective cohort study (GENE-RAD-RISK)," vol. 345, no. October, p. 2012, 2012; and D. Kardinah, B. O. Anderson, C. Duggan, I. Ali, and D. B. Thomas, "Short report: Limited effectiveness of screening mammography in addition to clinical breast examination by trained nurse midwives in rural Jakarta, Indonesia," *Int. J. Cancer*, vol. 134, no. 5, pp. 1250-5, March 2014. Information about the lesion, such as size, is an important factor in stratifying risk, and mortality that is not considered in current screening practices. L. Ries, J. J. Young, G. Keel, M. Eisner, Y. Lin, and M.-J. Horner, "Cancer Survival Among Adults: US SEER Program, 1988-2001," *Patient Tumor Charact. Natl. Cancer Institute, SEER Program, NIH*, no. 07, 2007. By quantifying palpable masses and their changes over time, we intend to stratify risk and bridge the technology gap between BSE and mammography for palpable lesions.

Other imaging methods for screening exist, such as MRI and ultrasound, but are prohibitively expensive for population-wide screening and work best in conjunction with other screening methods. Experimental impedance measurement and thermography methods have been attempted but have never gained acceptance for use in a clinical setting due to low specificity. Tactile sensing methods to detect stiffer tissues based on mechanical properties have been developed and evaluated. For example, there is an FDA-cleared elastography technology system that uses a force sensor array in a hand-held system to characterize stiffer tissues. The commercial name of the system is SureTouch. See, M. Ayyildiz, B. Guclu, M. Z. Yildiz, and C. Basdogan, "A Novel Tactile Sensor for Detecting Lumps in Breast," pp. 367-372, 2010; V. Egorov, T. Kearney, S. B. Pollak, C. Rohatgi, N. Sarvazyan, S. Airapetian, S. Browning, and A. Sarvazyan, "Differentiation of benign and malignant breast lesions by mechanical imaging," *Breast Cancer Res. Treat.*, vol. 118, no. 1, pp. 67-80, November 2009; and A. Sarvazyan, V. Egorov, and N. Sarvazyan, "Tactile Sensing and Tactile Imaging in Detection of Cancer," in *Biosensors and Molecular Technologies for Cancer Diagnostics*, 2011, pp. 339-354. Another device, the Intelligent Breast Exam (iBE) system, uses a piezoelectric force sensor array to detect changes in mechanical properties of tissues. X. Xu, C. Gifford-Hollingsworth, R. Sensenig, W.-H. Shih, W. Y. Shih, and A. D. Brooks, "Breast tumor detection using piezoelectric fingers: first clinical report," *J. Am. Coll. Surg.*, vol. 216, no. 6, pp. 1168-73, June 2013. Both devices share a similar method and subsequent flaw: the resolution of the device is limited by the number or density of force sensors in the array. Tracking changes in shape or size with these devices would be either expensive to fabricate a probe with high sensor density, or insensitive. Furthermore, neither device is intended for use by a patient. A device that is inexpensive, user-friendly, and that can be used in the home would allow more frequent measurements with fewer clinical visits.

While it is evident that experts disagree about the balance between advantages and drawbacks to each mammographic and BSE screening procedures, there is general agreement that complimentary methods of lesion assessment to improve clinical outcomes are desirable. An opportunity exists for non-invasive and inexpensive evaluation of palpable lesions through tactile sensing. Existing devices fail to provide the basis for a model that includes both home and clinical monitoring over time.

SUMMARY

In view of the forgoing, the present disclosure is directed to devices and methods for characterization of structures in subcutaneous tissues. These devices and methods address the shortcomings in breast self-examination (BSE) and mammographic screening practices by, for example, enhancing the roles of patient and primary care physicians in the breast screening process. In particular, the use of these device and methods to characterize masses that are initially identified through conventional BSE will reduce the incidence of unnecessary tests, while encouraging further evaluation when needed. Therefore, the present disclosure relates to devices and methods that allow for affordable tracking of palpable mass characteristics over time. These devices and methods could replace the current screening paradigm while, in other cases, could build on established screening techniques.

The devices and methods of the present disclosure have significant potential for the screening of breast cancer in developed areas as an adjunct and/or alternative to mammography and home screening. In developing regions, the devices and methods of the present disclosure have the potential to provide an alternative process for evaluating lesions where mammography is not available. Further, the devices and methods of the present disclosure can be applied to additional areas, such as lymph node assessment or the quantification of other palpable structures. Patients with recurring fibrocystic disease in particular may benefit from a device that can help track and evaluate numerous masses over time.

In view of the forgoing, non-limiting examples of the embodiments will now be described.

According to an aspect of the disclosure, a palpation device includes: a frame formed from a substantially rigid material and comprising an opening; a tonometric lens extending through the opening of the frame and being configured to at least partially impinge a tissue of interest to identify an object embedded therein; and a radiation source. The lens comprises a body having a reflective coating on an outer surface thereof. The radiation source is positioned to illuminate the reflective coating such that a topography of the coating can be observed. The body includes a body material that is as stiff or stiffer than the tissue of interest and less stiff than the embedded object.

In certain configurations, the palpation device further includes a force sensor configured to measure force applied by the lens to the tissue. The force sensor can be mounted between the lens and frame, and comprises, e.g., one or more of a strain gauge and a piezoelectric transducer.

In certain configurations, the radiation source emits visible light, and the body of lens includes a curved profile. In one aspect, the body material includes a material having a Shore hardness of between 00-16 and 00-32. For example, the tissue of interest can be breast tissue and the object comprises a lesion embedded in the breast tissue.

In certain configurations, the reflective coating comprises fine particles including one or more of mica, iron oxide, titanium dioxide, silver, aluminum, gold, platinum, chrome, nickel, Inconel, titanium nitride, zinc oxide, copper, zinc, stearic acid, titanium dioxide, clay, calcium carbonate, silica, and talc. In an additional embodiment, an optically clear cover extends across the opening of the frame, and the body of the lens is at least partially mounted to the cover. Optionally, the body of the lens includes an optically clear material.

In certain configurations, the radiation source includes a first radiation source emitting radiation having a first wavelength and a second radiation source emitting radiation having a second wavelength, wherein that the first wavelength is different from the second wavelength. Optionally, a single radiation source can be configured to emit radiation of multiple wavelengths.

According to another aspect of the disclosure, a system for palpating a tissue to identify an object embedded therein is provided. The system includes a palpation device in communication with an image device. The palpation device includes: a frame formed from a substantially rigid material and comprising an opening, and a tonometric lens extending through the opening of the frame and being configured to at least partially impinge a tissue of interest to identify an object embedded therein. The lens includes a body having a reflective coating on an outer surface thereof. The image device is connected to or in communication with the palpation device. The image device includes: at least one optical sensor positioned to obtain an image of the topography of the coating through the tonometric lens, and a processor. The processor is configured to: receive at least one image from the optical sensor, process the image to identify an area of interest in the image, and provide feedback regarding the image and/or the area of interest. The body of the lens includes a body material that is as stiff or stiffer than the tissue of interest and less stiff than the embedded object.

In certain configurations, the optical sensor includes a video camera. Optionally, the coating includes fine particles including one or more of mica, iron oxide, titanium dioxide, silver, aluminum, gold, platinum, chrome, nickel, Inconel, titanium nitride, zinc oxide, copper, zinc, stearic acid, titanium dioxide, clay, calcium carbonate, silica, and talc.

In certain configurations, the palpation device includes a force sensor configured to determine a force that the palpation device applies to the tissue of interest. Processing the image can include identifying a displacement of the lens at the area of interest, and calculating a stiffness for the area of interest based, at least in part, on the calculated displacement and the force. Further, the processor can be configured to calculate a stiffness for multiple points on the image to provide a stiffness map for the tissue in the image.

In certain configurations, the system includes a location identification sensor for identifying a location of the palpation device on the body of the patient. The system can also include a visual display configured to provide an image from the image device. The image device can include a smart phone, personal data accessory, tablet PC, laptop computer, or any combination thereof. In some configurations, a light transmission cable extending between the image device and the palpation device is provided for conveying a field of view of the tonometric lens to the image device.

According to another aspect of the disclosure, a method for palpation of tissue of a patient for identification of an object embedded therein is provided. The method includes: applying a palpation device comprising a tonometric lens to tissue to at least partially impinge a tissue of a patient; identifying a topography of the tonometric lens once the lens is applied to the tissue; and identifying an object embedded in the tissue based, at least in part, on the topography of the lens.

In some implementations, the tonometric lens includes a body having a reflective coating on an outer surface thereof. The body of the lens can also include a body material that is as stiff or stiffer than the tissue and less stiff than an embedded object.

In some implementations, the method further includes determining a force that the lens of the palpation device applies to the tissue. The method can also include calculating a stiffness for a portion of the tissue, the stiffness being based on a displacement of the tissue and the force.

In some implementations, the method can include identifying a stiffness at multiple locations on the topography of the tissue and creating a map illustrating differences in the stiffness based on the identified stiffness at multiple locations.

In some implementations, the method can include tracking the stiffness of a tissue relative to itself over time rather than relative to adjacent tissues to quantify changes.

In some implementations, the method can include illuminating the coating of the lens with a radiation source located on the palpation device.

BRIEF DESCRIPTION OF THE DRAWINGS

These and other features and characteristics of the present disclosure, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limit of the invention.

Further features and other examples and advantages will become apparent from the following detailed description made with reference to the drawings in which.

DETAILED DESCRIPTION OF THE INVENTION

Figure 1A:
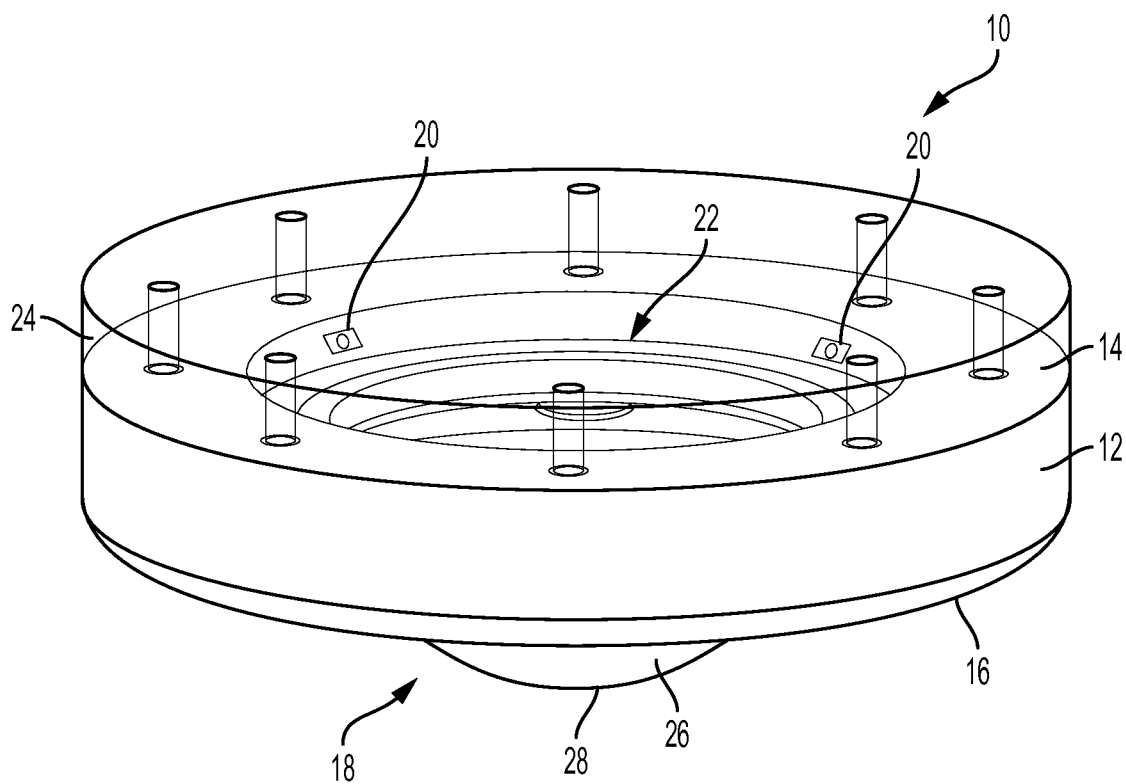
FIG. 1A is a perspective view of a palpation device including a tonometric lens for palpation of tissues for characterization of subcutaneous structures, according to an aspect of the disclosure.

As used herein, the singular form of "a", "an", and "the" include plural referents unless the context clearly dictates otherwise.

As used herein, the terms "right", "left", "top", and derivatives thereof shall relate to the invention as it is oriented in the drawing figures. However, it is to be understood that the invention can assume various alternative orientations and, accordingly, such terms are not to be considered as limiting. Also, it is to be understood that the invention can assume various alternative variations and stage sequences, except where expressly specified to the contrary. It is also to be understood that the specific devices and processes illustrated in the attached drawings, and described in the following specification, are examples. Hence, specific dimensions and other physical characteristics related to the embodiments disclosed herein are not to be considered as limiting.

Unless indicated to the contrary, the numerical parameters set forth in the following specification and attached claims are approximations that can vary depending upon the desired properties sought to be obtained by the present disclosure.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

Also, it should be understood that any numerical range recited herein is intended to include all sub-ranges subsumed therein. For example, a range of "1 to 10" is intended to include any and all sub-ranges between and including the recited minimum value of 1 and the recited maximum value of 10, that is, all subranges beginning with a minimum value equal to or greater than 1 and ending with a maximum value equal to or less than 10, and all subranges in between, e.g., 1 to 6.3, or 5.5 to 10, or 2.7 to 6.1.

As used herein, the terms "communication" and "communicate" refer to the receipt or transfer of one or more signals, messages, commands, or other type of data. For one unit or component to be in communication with another unit or component means that the one unit or component is able to directly or indirectly receive data from and/or transmit data to the other unit or component. This can refer to a direct or indirect connection that can be wired and/or wireless in nature. Additionally, two units or components can be in communication with each other even though the data transmitted can be modified, processed, routed, and the like, between the first and second unit or component. For example, a first unit can be in communication with a second unit even though the first unit passively receives data, and does not actively transmit data to the second unit. As another example, a first unit can be in communication with a second unit if an intermediary unit processes data from one unit and transmits processed data to the second unit. It will be appreciated that numerous other arrangements are possible.

The disclosure is generally directed to a cost-effective, sensitive, easy-to-use palpation aid that visually differentiates healthy from diseased tissue based on mechanical stiffness. As will be discussed in detail herein, the platform technology of the device is based a tonometric lens, which can be constructed from, for example, a soft, deformable, and optically clear material having a reflective coating or pattern on its convex surface. When the user palpates tissues with the device, subcutaneous structures of stiffer calcified or cancerous tissues are readily visible.

This device and method of use disclosed herein are intended to equip the PCP with a sensitive visualization tool to detect and track the size, shape, stiffness and location of a palpable mass, e.g., a palpable breast mass. These devices and methods both improve the accuracy/specificity of diagnosis, and provide options for tracking low-risk masses to reduce needless biopsies. These devices and methods also assist the PCP with risk stratification, so that the PCP only refers the patient to a specialist when needed. Because the present invention employs the principle of operation of palpation, its use is simple and intuitive for patients and primary care physicians alike. Further, because of the low cost of these devices, it is feasible for a patient to use it at home for tracking the progression, in collaboration with her doctor.

In some examples, the device can be integrated with or connected to a multipurpose electronic device, such as a personal data assistant, tablet PC, or smart phone, so that the visualized lesions may be recorded by camera and image processing may quantify the lesion's size and shape, and the history can be archived for offline review or transmission to a physician.

As will be discussed hereinafter, the device can include two subsystems: a sensor assembly, referred to hereinafter as the palpation device, and a camera-readout/processor assembly, referred to hereinafter as an image device. In some examples, the palpation device and the image device are coupled together, and can, for example, be enclosed within the same housing or frame. Alternatively, the palpation device and the image device can be physically separate or separable elements that communicate through wired or wireless communications circuitry. In still other examples, the palpation device can include electronic circuitry for image capture and initial processing. Following initial processing, information from the palpation device can be sent to another electronic device for further processing, analysis, or to provide feedback to a user or patient. In other examples, the palpation device can be used alone. In that case, a user can manually visually examines a field of view of the device to analyze tissue being examined Example Palpation Device:

With reference to FIGS. 1-3B and 6A-7, a device for palpation of tissues for characterization of subcutaneous structures (referred to as palpation device 10) is illustrated. Use of the device 10 can involve similar principles to palpation with human fingers to determine subcutaneous structures. As a human can feel boundaries between different mechanical properties of tissues during palpation, the device 10 visualizes these mechanical differences.

The palpation device 10 can be used for a number of different clinical processes. For example, the device 10 can be used for detecting heterogeneity of stiffness within a compliant object, including, for example, features for application of a distributed surface traction over a region, such as a region that is principally normal to the surface of the object. In another example, the device 10 can be used for mapping heterogeneity of stiffness of an object. In another example, the device 10 can be used to identify and visualize healthy tissue structures to identify structural changes or remodeling. In another example, the device 10 can be used for detecting an embedded lesion including compressing tissue at an applied force, causing a topographical disturbance in the superficial structure (topography) of said tissue, wherein the disturbance is proportional to the relative stiffness of the lesion, and estimating the size and/or shape of the lesion based on the applied force and magnitude of the topographical disturbance. As used herein, in some examples, a lesion is a pathological or benign change in the tissue of an organism, such as a tumor, cyst, abscess, or nodule, which results in a differing stiffness from adjacent tissues. In other examples, a lesion can be a gap, wound, or other injury.

The palpation device 10 includes a frame or housing 12 having an upper surface 14 and a lower surface 16, a tonometric lens 18 extending through a portion the housing 12, and one or more radiation sources 20. In some examples, the frame 12 is an annular structure including a central opening 22 that receives the tonometric lens 18. The opening 22 can also form a window for viewing a field of view of the lens 18. A backing plate or cover 24, such as a plate formed from a transparent acrylic or polymer material, can be mounted to and extend across the upper surface 14 of the housing 12. The cover 24 can be mounted to the housing 12 using adhesives and/or mechanical fasteners, such as screws or clips, as are known in the art.

Figure 1B:
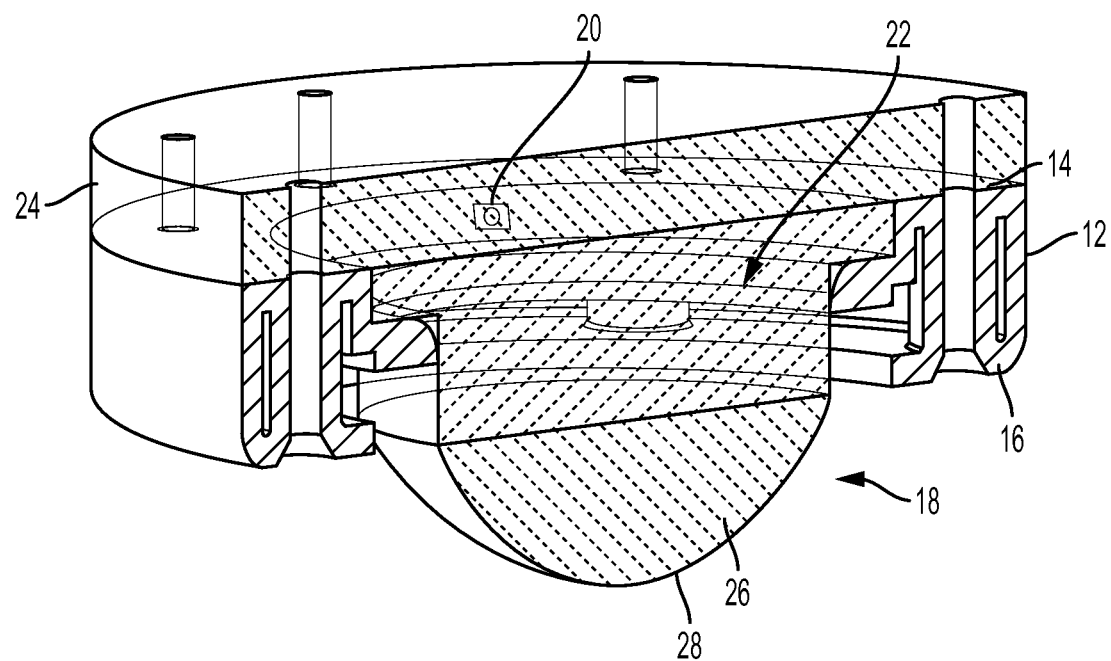
FIG. 1B is a cross section view of the palpation device of FIG. 1A.

The tonometric lens 18 includes a substantially deformable body 26 mounted to the cover 24 and/or housing 12. The body 26 is configured to extend from the central opening 22 of the housing 12, and is positioned to contact the tissue to be characterized. The body 26 is generally formed from a flexible and deformable material, such as an elastomer gel. The gel can be formed by heat-forming process, and provided with a Shore hardness (durometer) of between about 00-16 and 00-32. An exemplary gel material is a thermoplastic elastomer, such as the Versaflex™ family of thermoplastic elastomers manufactured by GLS Corporation, the family of Dermasol thermoplastic elastomers by California Medical, or the Ultraflex series from Douglas & Sturgess. Other materials can include silicone polymers including Polydimethylsiloxane (PDMS), polyurethane, or hydrogels, such as polyvinyl alcohol cryogels (PVA). The stiffness of the material is selected to be within a range between the stiffness of the tissue being examined (e.g., breast tissue) and the anticipated stiffness of the lesion or mass to be identified. Breast tissue can have a Young's modulus of approximately 1.5-60 kPa for healthy tissues, and up to approximately 200 kPa to 300 kPa for pathological breast tissue. In a non-limiting example, the body 26 has a curved profile and, for example, can be a hemisphere, as shown in FIG. 1B. However, the shape of the body 26 can be selected to increase deformation for the purpose of enhancing resolution of the lens 18. The body 20 material is generally optically clear and/or transparent so that a user or image sensor can see or otherwise image displacement of the outer surface of the body 26 when it is compressed against tissue.

The body 26 is coated with a coating 28 formed from a layer of fine, reflective particles. The coating 28 is provided on the outer surface of the body 26 and comes into contact with the tissue of interest. For example, the coating 28 can be formed from fine reflective particles of mica, iron oxide and titanium dioxide. Other examples of reflective materials include: silver, aluminum, gold, platinum, chrome, nickel, Inconel particles; titanium nitride or zinc oxide; copper. Zinc, stearic acid, titanium dioxide, clays, calcium carbonate, silica, talc, or any other pigment that can reflect either visible or UV light can also be used.

With continued reference to FIGS. 1A-3B and 6A-7, the radiation source 20 is configured to illuminate the reflective coating 28, such that a topography of the coating 28 is visible through the lens 18. The radiation source 20 can be a light emitting diode (LED) that emits either a single wavelength or multiple wavelengths of radiation. Radiation sources 20 emitting radiation in the non-visible spectrum (e.g., ultraviolet or infrared radiation) can be used for specific applications. In some examples, the coating 28 exhibits known, diffuse reflective properties when exposed to radiation from the radiation source 20, so skin color does not affect the sensitivity of the lens 12.

In use, the user presses the distal end of the tonometric lens 18 against a tissue to be characterized. When the user presses the tonometric lens 18 against the tissue, the body 26 of the lens 18 compresses, which forces the coating 28 to conform to topography of the tissue surface. Upon increasing pressing force, the body 26 at least partially impinges upon the tissue. As a result, the compressed body 26 conforms to the shape of certain subcutaneous structures having a stiffness greater than the surrounding tissue. Thus, the shape of the subcutaneous structures can be seen through the lens 18. More specifically, changes in the topography of the coating 28 cause variations in reflected light relative to the surface normal of the subject tissues. The radiation source 20 is used to illuminate the coating 28 to make changes in topography easier to identify. As discussed herein in connection with the image device (shown in FIGS. 6A-9) an image sensor, such as a camera, can be used to record an image of the topography of the tissue, as shown by the coating 28, for analysis.

In some examples, the radiation source 20 can use multiple wavelengths of light to increase the accuracy of three-dimensional mapping and/or uses of infrared radiation (IR)

for heat mapping in addition to structural mapping. Using illumination with multiple wavelengths of light enhances the diagnostic capacity of the device 10 in the case of cancerous lesions with a clinical presentation of increased blood flow in the region. In other examples, the device 10 includes multiple radiation sources 20 to illuminate the coating 28 from different angles. Different angles of illumination can be used to produce a representation of a stereo-image, which can be used to identify or provide a more accurate estimate of relative distance in the capture images.

Figure 7:
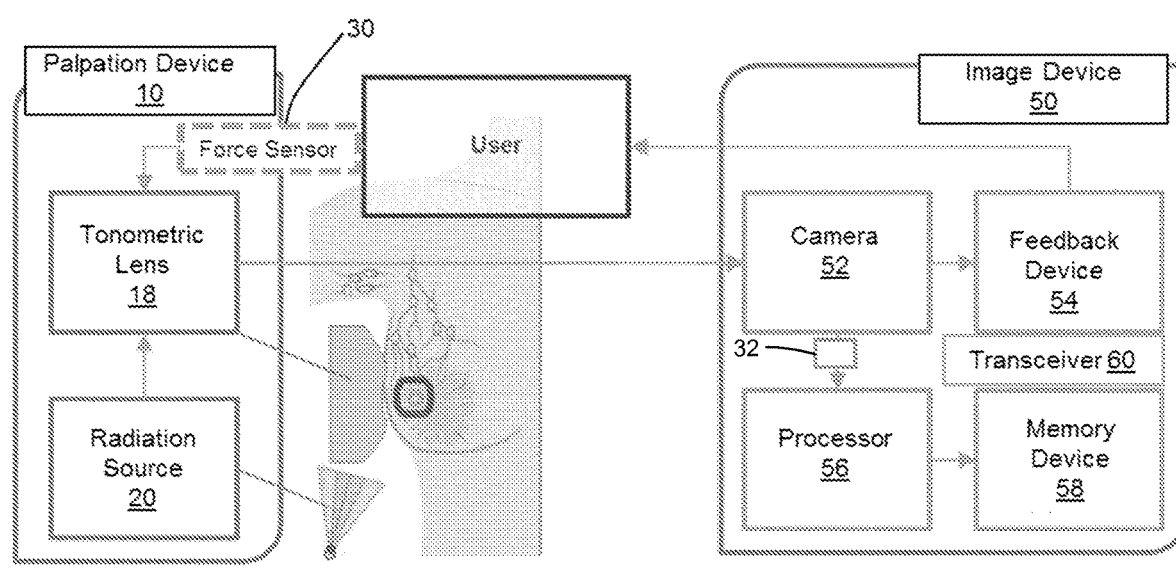
FIG. 7 is a schematic drawing of the devices of FIG. 6A.

With specific reference to FIG. 7, the palpation device 10 can also include a force sensor 30. The force sensor 30 can be configured to determine the amount of force exerted by the device 10 against the tissue to be characterized. For example, the force sensor 30 can be interposed between the lens 18 and the fame 12 (shown in FIGS. 1A and 1B) or between the lens 18 and the cover 24 (shown in FIGS. 1A and 1B). The force sensor 30 can be a strain gauge, piezoelectric transducer, or other electronic or mechanical sensor as is known in the art.

As is discussed in greater detail herein, the relative stiffness of the tissue can be estimated based on the ratio of the deformation ($\delta_T$ in FIG. 3B) to the force. Actual stiffness can be calculated by determining an amount of force with the force sensor 30 that produces an amount of deformation, as identified by deformation of the body 26. A map of a stiffness field can be determined by inversion of the equations of elasticity, using the full topographic map of the surface rather than the height of the deformation at a specific location.

In another example, the force can be estimated by incorporating gas bubbles into the body 26 of the lens 18. The bubbles can be a known size when no force is applied to the lens (e.g., when the lens is not in contact with the tissue to be characterized). When the device 10 is pressed against the tissue, compression of the bubbles can be visualized contemporaneous with the topography of the reflective coating 28. The resulting change in size or shape of the gas bubbles can be translated to force, based on prior calibration.

In other examples, the device 10 can include a location sensor 32 for tracking the location of the palpation device 10 on the tissue. For example, the location sensor 32 can be a laser, accelerometer, or gyroscope, which can be used to identify a specific or relative position of the device 10 on the patient. An image obtained from the device 10 can be marked with its location, as determined by the location sensor 32. By documenting the location for each image, a complete mapping of the subject tissues, and mechanical properties thereof can be determined. Such a map of tissue stiffness can be used to improve the detection of tissue abnormalities by establishing a baseline for the mechanics of local tissues.

Figure 2:
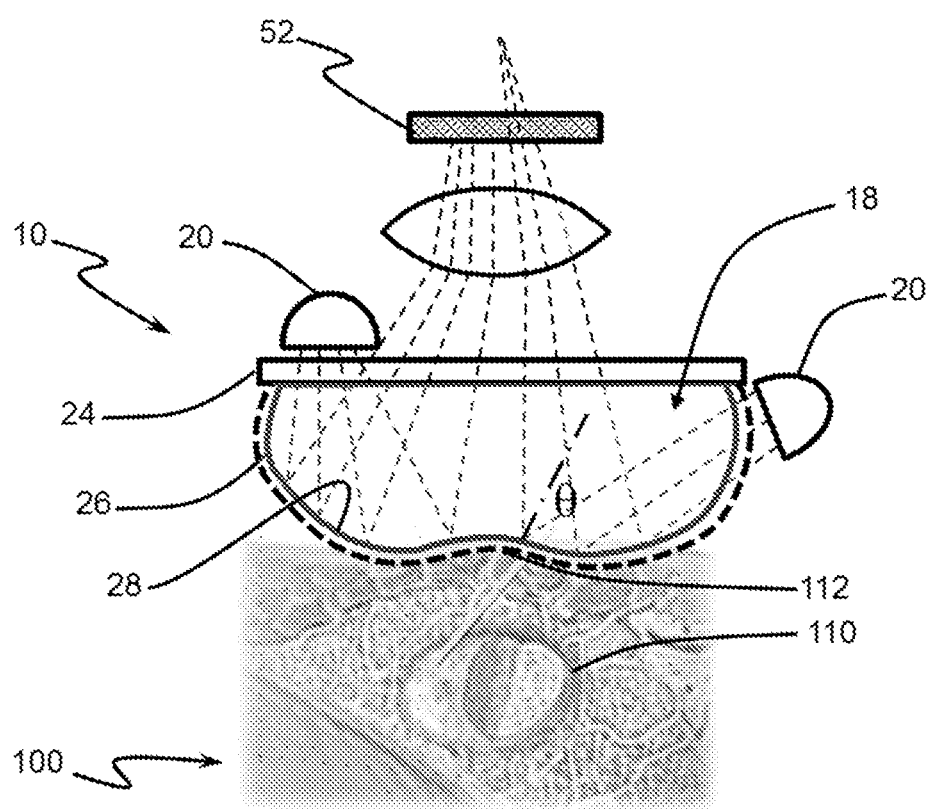
FIG. 2 is a schematic drawing of the device of FIG. 1A pressed against tissue containing a lesion.

Use of a Tonometric Lens:

With reference to FIG. 2, the tonometric lens 18 is illustrated in contact with and impinging upon a tissue to be characterized, such as breast tissue 100. In this example, a user can palpate the breast tissue 100 with the lens 18 and observe the presence and approximate size and shape of any lesions 110 as a disturbance 112 within the field of view of the lens 18. It can be appreciated that lesions of varied shapes, depths, and motilities within the tissue may be identified in a similar manner.

Figure 3A:
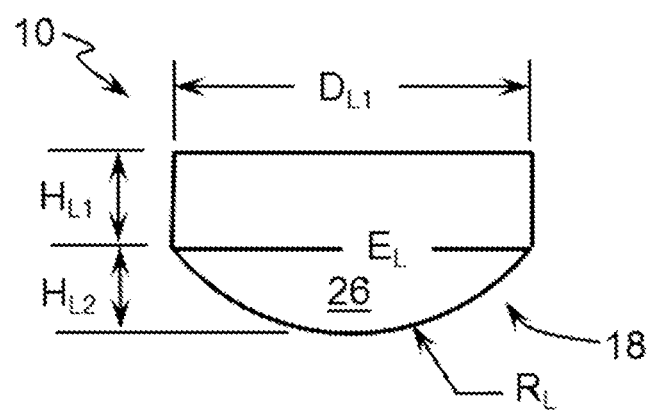
FIGS. 3A and 3B are schematic drawings of the tonometric lens of the device of FIG. 1A, and illustrating geometric features of the lens and/or device.
Figure 3B:
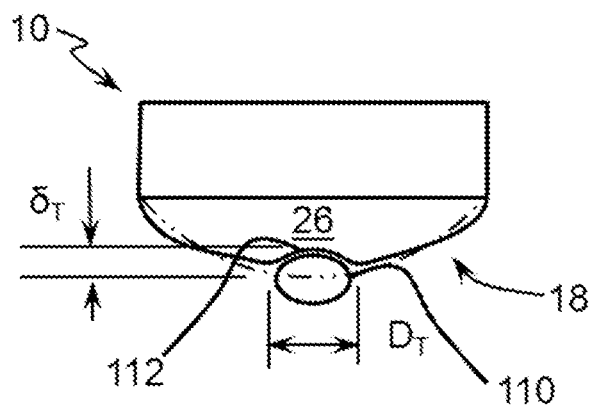

With reference to FIGS. 3A and 3B, diagrams illustrating primary geometric features of the tonometric lens 18 are provided. With respect to the lens 18, the stiffness and geometry are such that, when pressed against the breast, the lens 18 produces a pronounced topographic disturbance in its contour. An increase in the amount of topographic disturbance results in increased optical signal (contrast). If the body 26 material is too stiff, it may require excessive force to deflect the lens 18, possibly flattening the lesion 110. If the lens 18 is too soft, it will not provide sufficient force to deform the healthy tissue surrounding the lesion 110. This biomechanical problem is a function of both stiffness and shape, with the primary independent variables being the radius of curvature $R_L$, height $H_{L2}$, diameter $D_{L1}$, and modulus of elasticity $E_L$. In one non-limiting example, the diameter, $D_{L1}$, is 45 mm. As shown in FIG. 3B, the lesion 110 produces the disturbance 112 in the topography of the lens 18. The deformation of the lens 18 is identified as $\delta_T$.

FIGS. 4A-4D are diagrams illustrating the calibration relationships between lesion size ($D_L$), estimated size from image segmentation (Dseg), elasticity/stiffness, and applied force. In some examples, calibration is performed by compressing the lens against solid phantom until completely conformal, indicated by point (force) at which the image no longer changes, resulting plot of segmented image versus known diameter of lesion to provide a calibration curve.

Figure 4A:
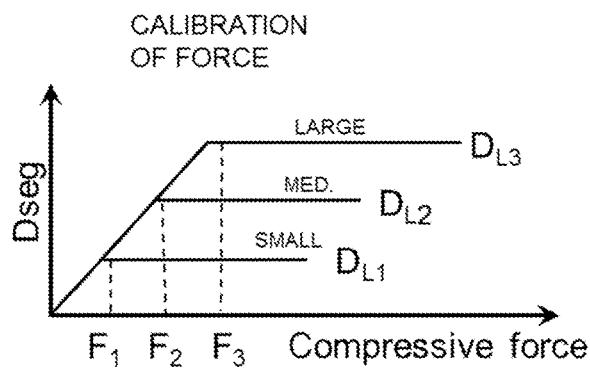
FIGS. 4A-4D are diagrams illustrating calibration relationships between lesion size ($D_L$), estimated size from image segmentation ($D_{Seg}$), elasticity/stiffness, and applied force.
Figure 4B:
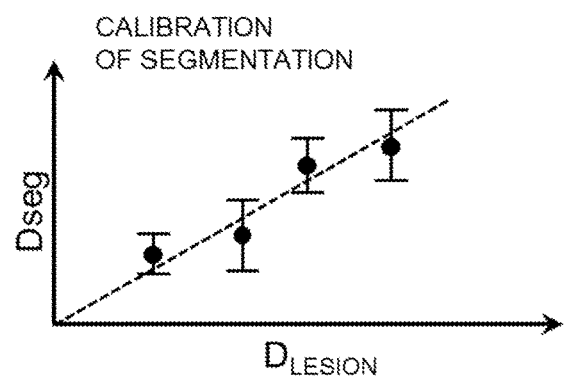
Figure 4C:
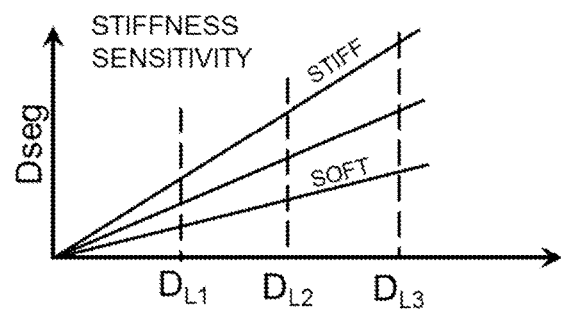
Figure 4D:
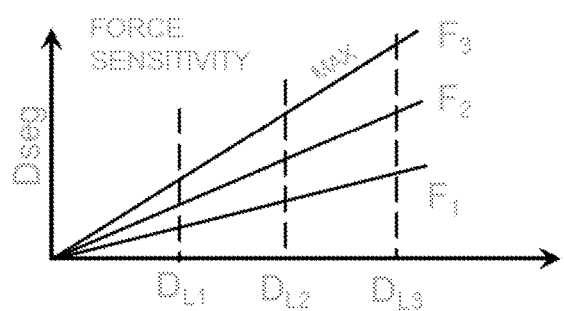

More specifically, FIG. 4A depicts an estimator for force, which illustrates that as the lens is applied with increasing force, the detected segmented area will reach a threshold. The threshold is dependent on the size of the lesion ($D_L$). FIG. 4B is representative of an offline calibration between actual size of lesion, and estimated size from segmentation algorithm. FIG. 4C is an offline calibration of segmented area versus lesion area for a given level of force. FIG. 4D indicates a mapping of $D_L$ to $D_{SEG}$ as a function of force.

Figure 5A:
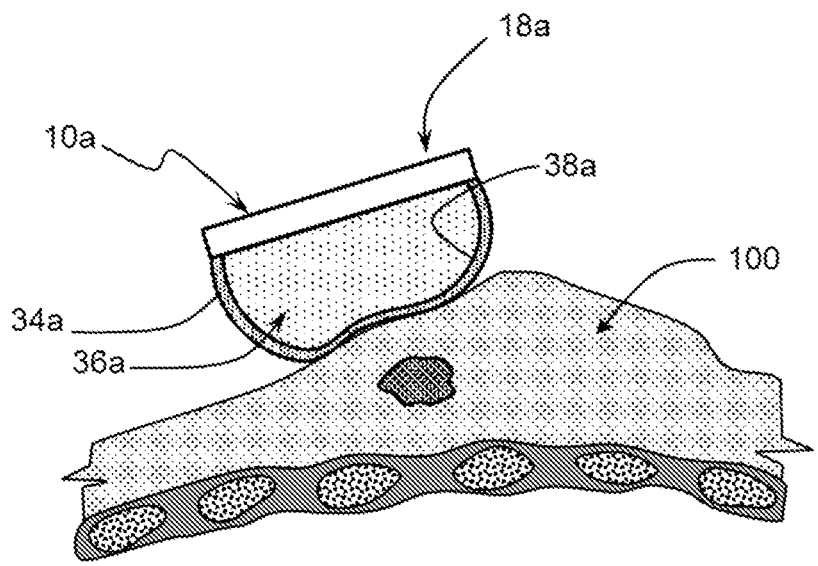
FIG. 5A is a schematic drawing of another example of a device for palpation of tissues for characterization of subcutaneous structures according to an aspect of the disclosure.
Figure 5B:
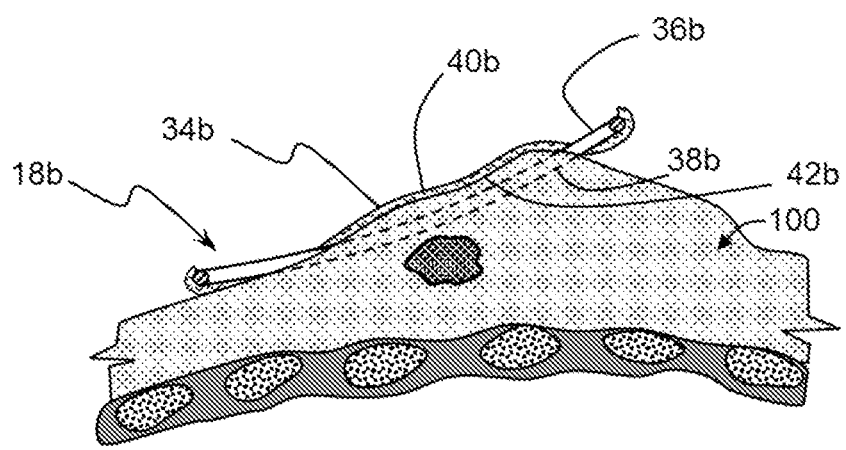
FIG. 5B is a schematic drawing of another example of a device for palpation of tissues for characterization of subcutaneous structures according to an aspect of the disclosure.

Additional Example Palpation Devices:

FIGS. 5A and 5B depict alternate embodiments of the tonometric lens 18a, 18b. With reference to FIG. 5A, the lens 18a includes a sac 34a filled with a fluid material 36a, such as a gel or gas, having reflective property. The portion of the sac 34a in contact with the tissue 100 can be reflective to increase visibility. The reflective portion may be a reflective coating 38a on the interior or exterior of the sac 34a. In other examples, the material of the sac 34a can itself be a reflective material. For example, the sac 34a can be formed from Mylar (e.g., Biaxially-oriented polyethylene terephthalate).

With reference to FIG. 5B, the lens 18b includes a membrane or fabric 34b supported by a rigid frame 36b. The frame 36b can be arranged in the shape of a bow to create a convex surface 38b that can be deformed when in contact with the tissue 100. The membrane 34b includes an upper surface 40b that, when the lens 18b is pressed against tissue 100, is visible (e.g., exposed to the user's eye or to an image sensor). A lower surface 42b of the membrane 34b is in contact with the tissue 100 being characterized.

Figure 6A:
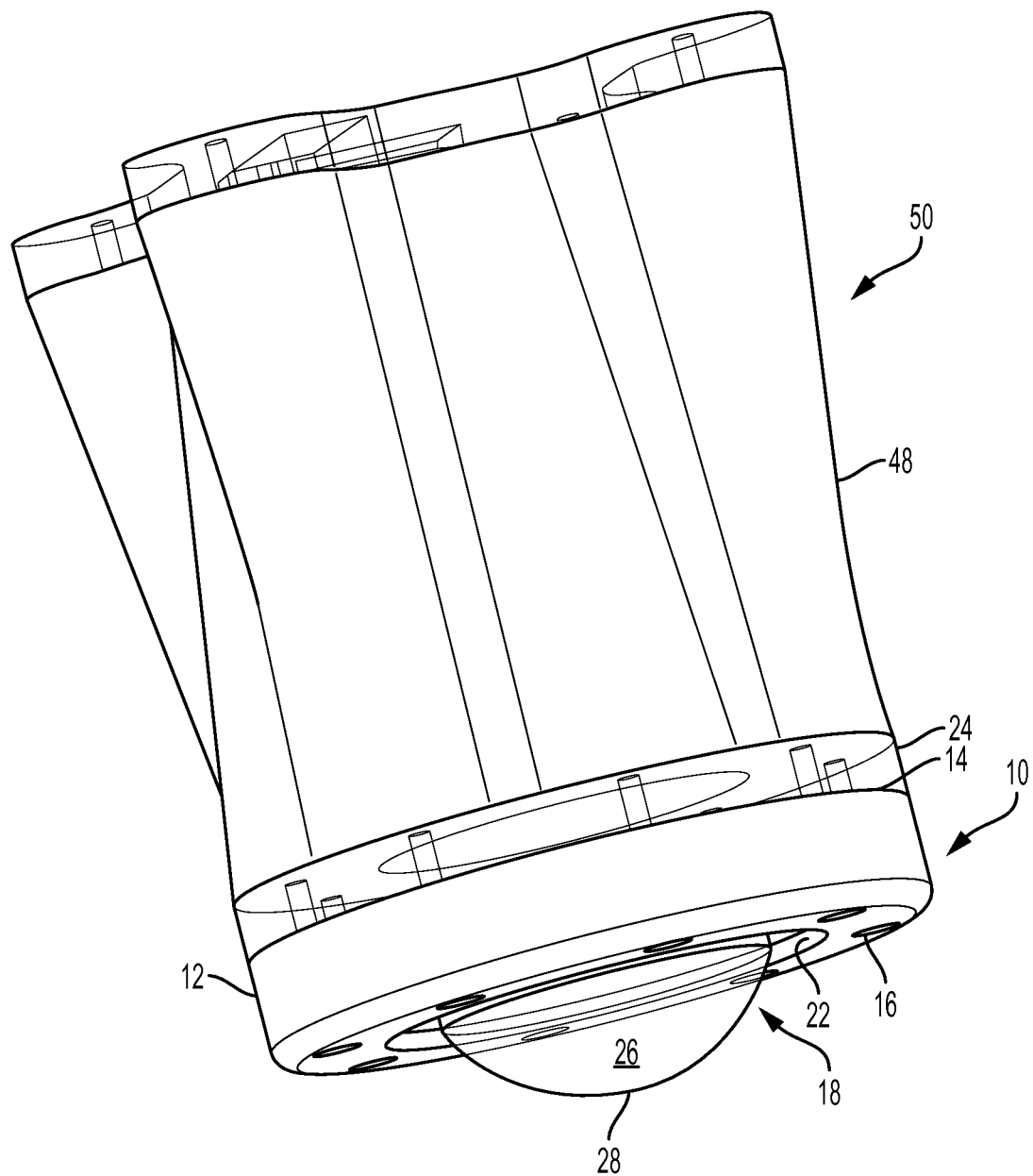
FIG. 6A is a perspective view of an image device in combination with the palpation device of FIG. 1A.
Figure 6B:
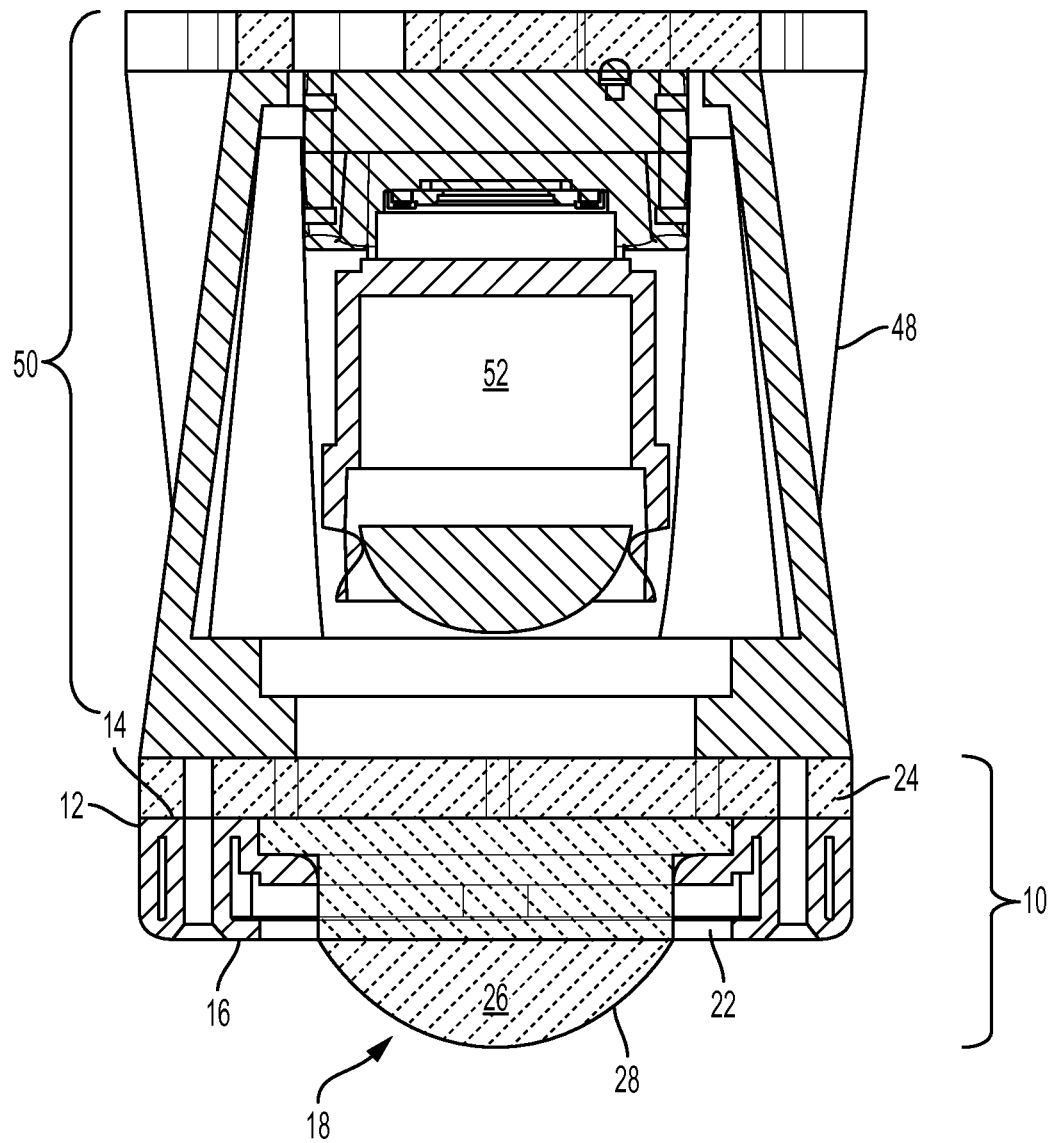
FIG. 6B is a cross section view of the image and palpation devices of FIG. 6A.

Example Image Device:

With reference to FIGS. 6A-7, the palpation device 10 is coupled to and/or in communication with an image device 50. The image device 50 is enclosed within a housing 48 (shown in FIGS. 6A and 6B) that can be connected to the frame 12 or cover 24 of the palpation device 10 by a mechanical fastener or clip. The image device 50 includes an optical sensor 52 to capture the topographical changes of the lens 18, which can then be displayed on a feedback device 54, such as a viewing screen. For example, as shown in FIG. 6B, the sensor 52 can be positioned within the housing 48 and above the central opening 22 of the frame 12 to provide a good view of the topography of the coating 28.

The optical sensor 52 can be a digital camera. Although designs from different vendors are different, a camera usually consists of a charge-coupled device (CCD) or complementary metal-oxide-semiconductor (CMOS) imaging sensor, a lens, a multifunctional video control chip, and a set of discrete components (e.g., capacitor, resistors, and connectors). The optical sensor 52 can be configured to obtain static or dynamic images based on the particular type of analysis or screening being performed.

With specific reference to FIG. 7, the image device 50 also includes or is in communication with a controller 56, such as a microprocessor, that receives an optical signal (e.g. an image) from the optical sensor 52, analyzes the optical signal, and, in some examples, converts the optical signal to a two-dimensional mapping of topography of the lens 18. The controller 56 includes or is in communication with computer readable memory 58, and, optionally, a data transceiver 60 for sending the optical signal and/or results of analysis by the controller 56 to an external source.

The computer readable memory 58 can include, for example, a digital data recorder such as a disk drive which records data onto a data storage medium. In another example, the data storage medium can be any type of non-volatile memory, for example, magnetic data storage media such as a hard disk drive or magnetic tape, or flash-based memory. Flash memory is a non-volatile computer storage chip using NAND or NOR type memory as found in MicroSD cards, USB flash drives, or solid-state drives. File systems optimized for flash memory (solid state media) include Embedded Transactional File System (ETFS), exFat and FFS2 systems. In other examples, the data storage medium can be random access memory (RAM) or read only memory (ROM). The memory may be removable from the device 50 or permanently installed within the device 50 and transferable to an external device through the data transceiver 60.

The data transceiver 60 can be configured to provide information from the image device 50 to the external source via a communications network. For example, networks may be wired, using, e.g., USB, Ethernet and FireWire protocols. In other examples, the data transceiver 60 can be in communication with a wireless network employing a wireless network technology such as Bluetooth, Wi-Fi, Z-Wave and ZigBee. Wi-Fi (e.g., IEEE 802.11a, b, g, n) networking protocols can also be used, which advantageously have a greater transmission range than a short range transmission network such as Bluetooth, but consequently also have greater power consumption. Suitable external sources for receiving data transmitted from the device and optionally providing additional processing for the received data include a computer, tablet PC, or another smart phone and/or an external hard drive or other device for backing up stored data. In addition, data can be received by a remote computer network or storage device for storage and/or for further processing and analysis.

With continued reference to FIG. 7, the controller 56 can be configured to execute software. A function of the software is to translate the topological mapping of the reflective coating and applied forces to estimate the mechanical properties of the palpated tissues. Simultaneously, automated lesion detection and segmentation of the image can be used to help the user easily identify and isolate a palpable mass.

A further function of the software is to record the image, topographic map, force, and/or the stiffness map for later display. Recording of sequential measurements provides a historical record of trends over the course of time.

Figure 12A:
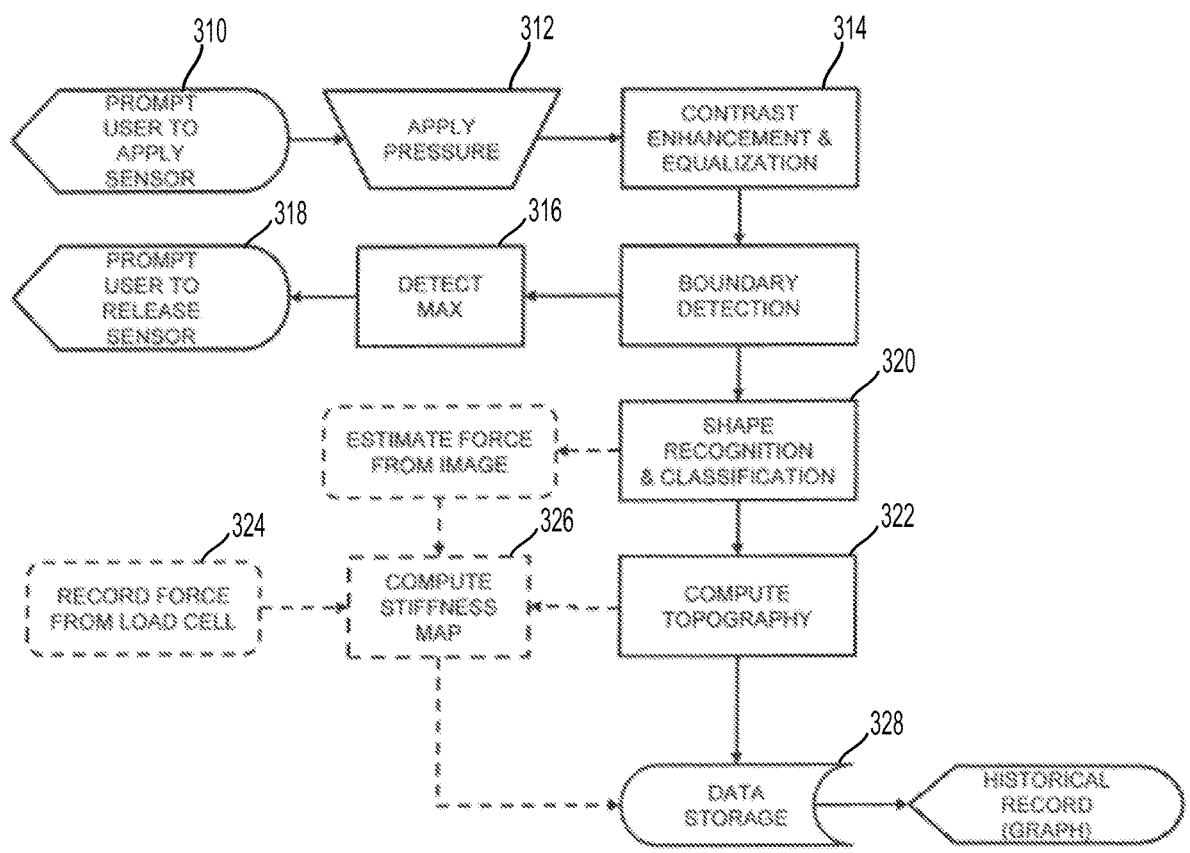
FIG. 12A is a flow chart showing steps for processing of an image obtained using the device of FIG. 1A.
Figure 12B:
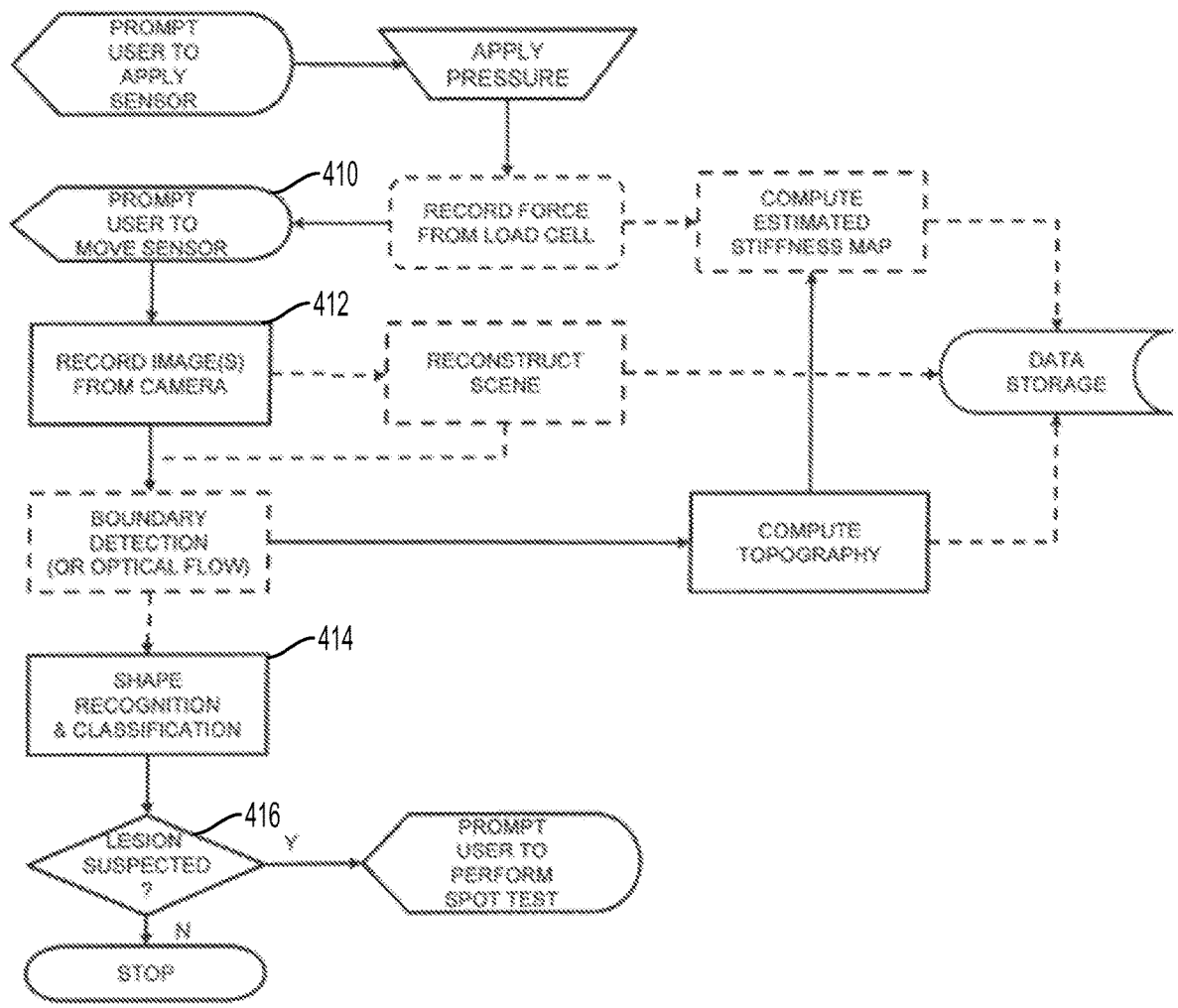
FIG. 12B is another flow chart showing steps for processing of an image obtained using the device of FIG. 1A.

In some cases, the controller 56 can also be configured to provide analysis for images obtained from the one or more optical sensors 52. In some examples, image processing (also referred to as computer vision), can be used to quantify the size and shape of the revealed lesion from the captured image. In some examples, image processing routines can include two components, namely image segmentation and machine learning. The former involves identification of the boundary between two domains, or the "edge" of an object. The latter involves classification or identification (like face recognition found in most digital cameras). FIGS. 12A and 12B provides two examples of image capture and processing routines that can be performed by the devices 10, 50.

Figures 8A, 8B:
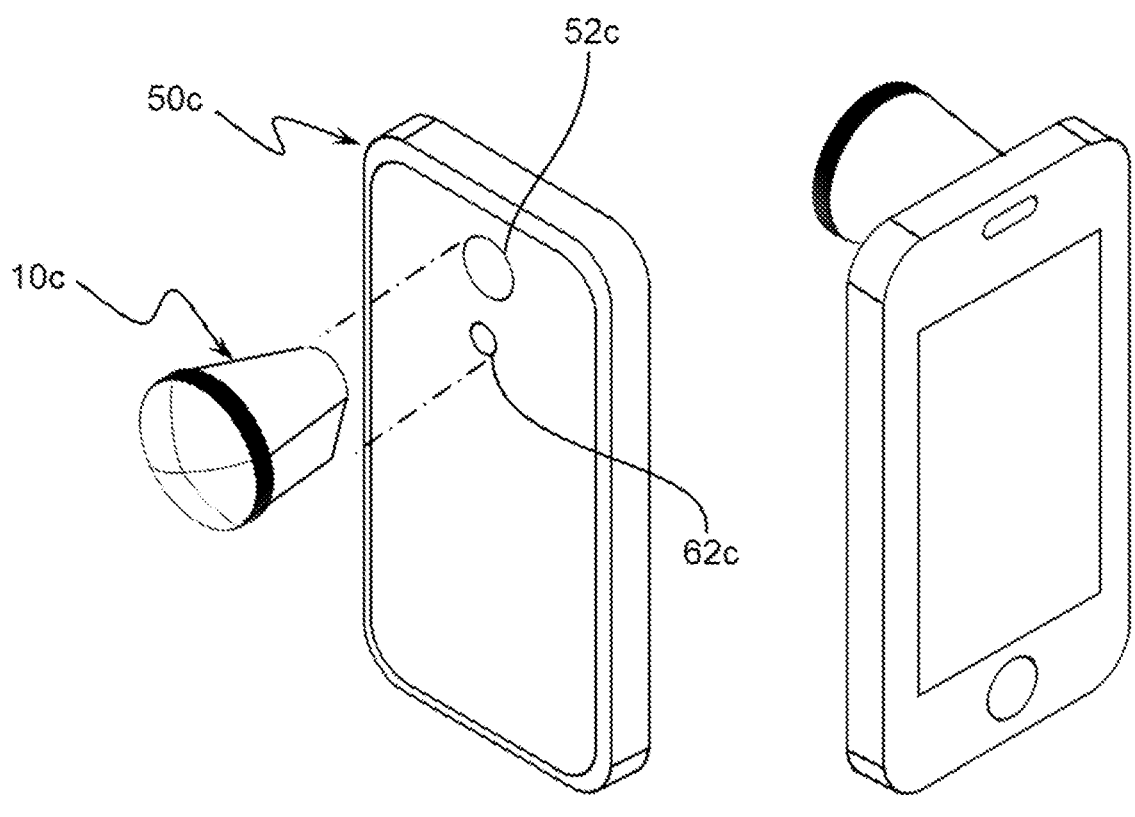
FIGS. 8A and 8B are perspective views of another embodiment of the palpation and image devices, according to an aspect of the disclosure.
Figure 9:
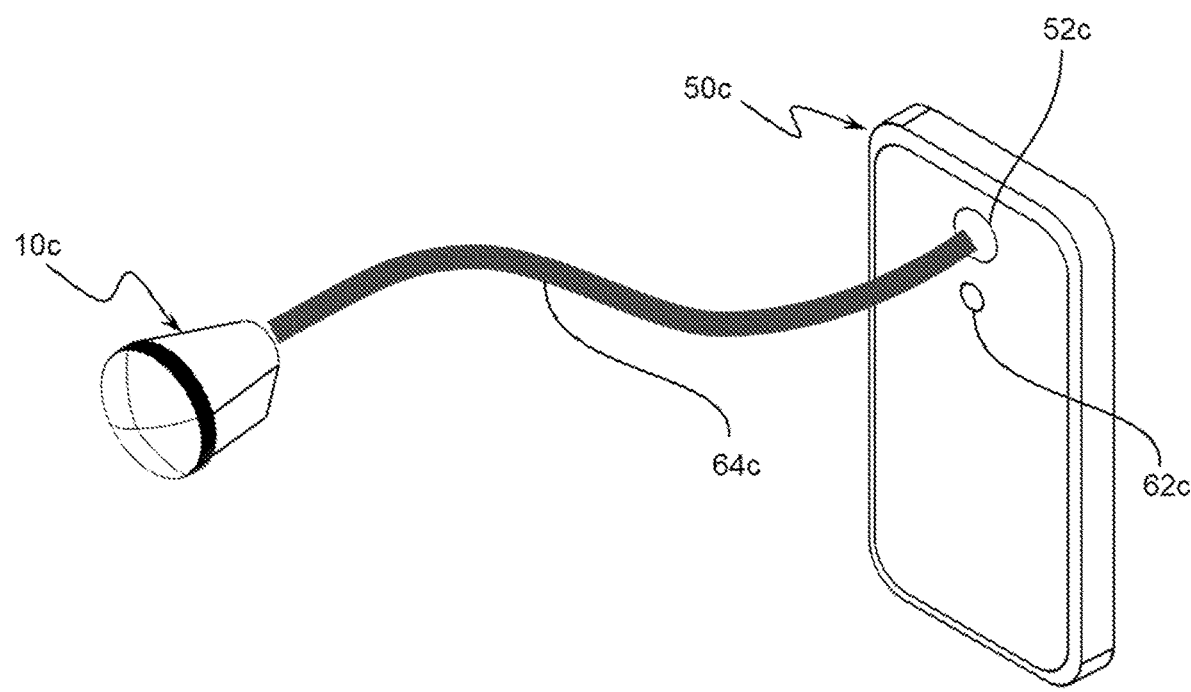
FIG. 9 is a perspective view of another embodiment of a palpation device and image devices, according to an aspect of the disclosure.

With reference to FIGS. 8A-9, another example of a palpation device 10c and image device 50c are illustrated. As shown in FIGS. 8A-9, the image device 50c is a multipurpose electronic device 50c, such as a smart phone, personal digital assistant (PDA), or tablet PC, including a camera 52c and radiation source 62c, such as a camera flash. The palpation device 10c is provided as an attachment to the multipurpose electronic device 52c. The radiation source 62c can be an LED source, as is found on commercially available smart phones and other electronic devices. It can be appreciated that the palpation device 10c can be attached to the multipurpose electronic device 50c by an attachment structure, such as adhesive, threaded connector, bayonet connector, clip or fastener. With reference to FIG. 9, in another example, the palpation device 10c is separate from the multipurpose electronic device 50c. In that case, the field of view of the lens 18 is provided to the camera 52c of the multipurpose electronic device 52ca by a light transmitting cable 64c, such as a fiber optic cable or light pipe.

With reference to FIGS. 10A-10D, the multipurpose electronic device 50 can include a user interface for reviewing images obtained from the palpation device and image device. For example, the user interface can include downloadable or non-downloadable software installed on the multipurpose electronic device 50 (e.g. "the application"). The application can be a multi-platform application configured to run on a desktop, tablet PC, or smart phone. In some examples, the application offers several functions, including automated image capture, computer recognition, anatomic registration, data logging, and communication with a physician.

Figure 10A:
FIGS. 10A-10D are schematic drawings of screen captures of a user interface for the device of FIGS. 8A-9.
Figure 10B:
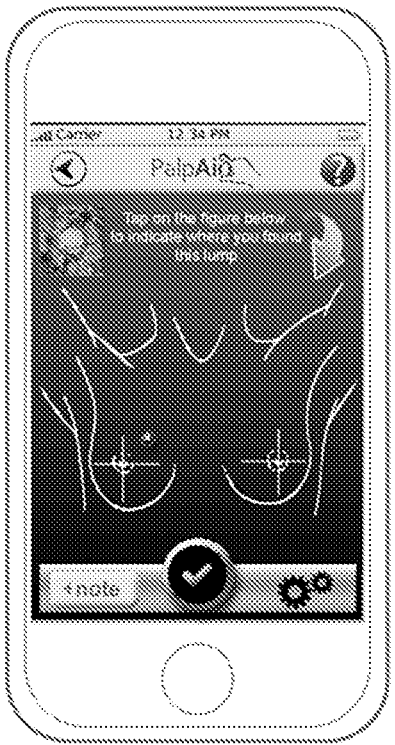
Figure 10C:
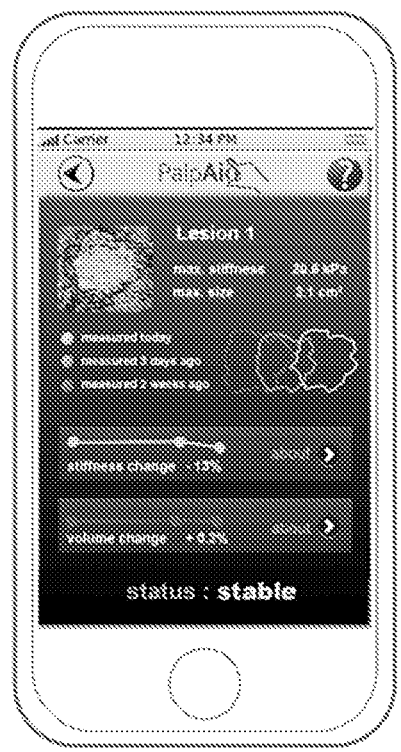
Figure 10D:

For example, as shown in FIG. 10A, the user interface can display an image obtained from the camera. In the displayed image, regions of increased stiffness appear in a lighter color. By identifying brighter areas on the image, a user can make an initial determination of the location of a subcutaneous structure of interest. As shown in FIG. 10B, the user can identify the location on her body where the structure of interest was identified. As shown in FIG. 10C, the user interface assists the user to monitor the size and stiffness of the identified structure over time (e.g., a lesion tracking function). For example, the user interface can be configured to record information about size and/or stiffness each time that a scan is performed using the device 10. The user interface can also include a scheduling component that alerts a user of when another scan should be performed. As shown in FIG. 10D, a lesion menu screen of the user interface is illustrated. The user screen presents options to the user such as, for example, an instruction to send information about the lesion to the user's doctor or to schedule an appointment with a doctor. From the lesion menu, a user can also select to continue tracking the lesion or to view lesion information stored on the device.

Figure 11:
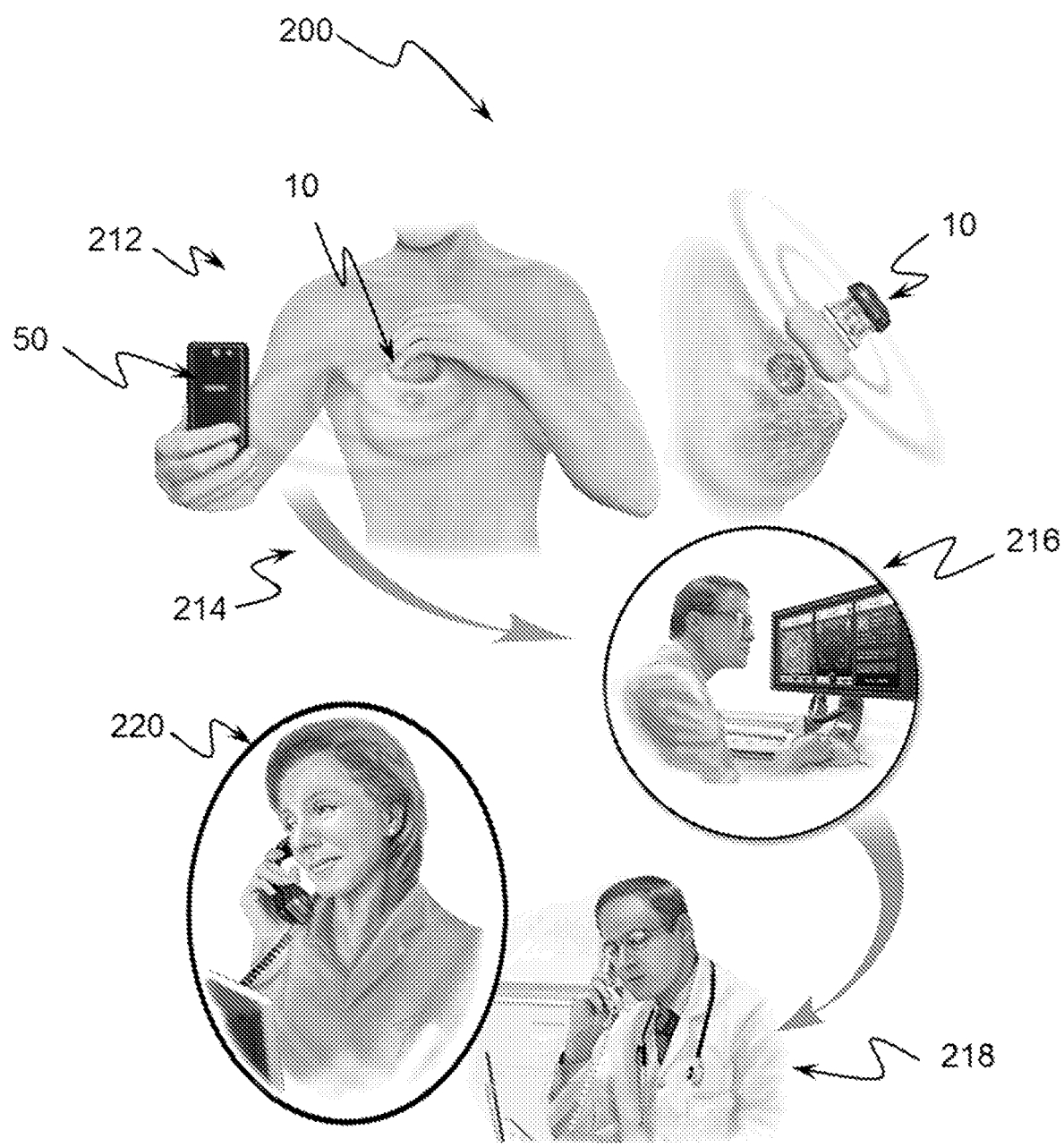
FIG. 11 is a schematic drawing of a system for tissue analysis including a device for palpation of tissues for characterization of subcutaneous tissues.

Example System for Identification and Reporting of Subcutaneous Structures:

Having described the palpation device 10 and image device 50, with reference to FIG. 11, a monitoring system 200 for obtaining information regarding subcutaneous tissues 100 from the image device 50 and for using the information for characterization of the tissue 100 is now discussed.

The system 200 can be configured for use with any of the above described palpation devices 10 and image devices 50. For example, as shown in FIG. 11, the image device 50 can be a multipurpose electronic device that is in wireless communication with a palpation device 10.

In use, as shown at 212, the patient applies the palpation device 10 to the tissue of interest in the manner discussed above. An optical signal representative of the topography of the lens 18 is obtained by the optical sensor or camera of the image device 50. The obtained optical signal can be displayed to the patient on the multipurpose electronic device and, as discussed above, can be stored in system memory. After a period of time, as shown at 214, the stored image can be sent (e.g. wirelessly transmitted) to an external source, such as a monitoring facility 216, technician, caregiver, researcher, or the patient's physician. In some examples, the obtained image is sent directly to the reviewer. In other examples, the image can be processed either on the device 50 or at the monitoring facility 216 prior to manual review by the reviewer. The reviewer can then prepare a report documenting any lesions or other abnormalities identified during processing of the data. The report can be in the form of an electronic document including relevant information, such as the patient name, ID number, health insurance information, as well as images analysis statistics, such as lesion size or change in lesion size over time. Statistics can also include a stiffness of the body tissue and identified abnormalities or comparison of results for different breasts. As shown at 218, the report is sent to a physician, caregiver, or other interested individual. After reviewing the patient report, as shown at 220, the physician has the option of contacting the patient to discuss the results. For example, the physician could instruct the patient to continue monitoring the identified structure using the lesion tracking feature described above. The physician can also contact other physicians to discuss the results.

Image Processing Method:

Having discussed the palpation device 10 and associated monitoring system 200, methods for using the device and for processing images obtained from the camera associated with the device 10 are now discussed in detail.

In one example and with reference to FIG. 12A, a static analysis method referred to as Spot Mode is illustrated. In this mode, as shown at box 310, the user is prompted to apply the tonometric lens to the breast tissue and, at box 312, to apply pressure to the lens. Once the lens is in place, an image is obtained and after preprocessing (by contrast enhancement and background subtraction as shown in box 314), static segmentation is performed. For example, static segmentation can be performed using image processing algorithms for Matlab software (The Mathworks, Natick, Mass.). Alternatively, preprocessing can be performed using phase congruency feature detection, available in an open source image processing library. A phase congruency feature detection algorithm that can be adopted for use with the devices and methods of the present disclosure is discussed in P. Kovesi, "Phase Congruency Detects Corners and Edges," pp. 10-12, 2003. This approach addresses the challenge of intensity phase gradients that are present in images obtained from a tonometric sensor. Optionally, multiple image segmentation and edge detection algorithms can be used in conjunction to create a more robust understanding of the lesion presence and size in the optical signal. Alternatively, a deformable pattern on the surface of the lens or via structured light approaches can provide data to the image sensor that can be interpreted into topography of the lens surface.

When sufficient force has been applied to the lens to reveal a lesion, the user is prompted to maintain the position of the lens on the breast and to continue increasing the level of force until the size of the segmented boundaries of the lesion cease to change, which is referred to as detecting a maximum lesion size as shown at box 316. Once the maximum image is obtained (e.g., an image of the lesion under sufficient force that the segmented boundaries of the lesion cease to change), at box 318, the user is prompted to release the lens. Once the maximum image is recorded, it may also be analyzed by an image classifier to identify the shape as shown at box 320, such as border irregularities indicative of the underlying pathology of the lesion. Information from the obtained image can also be used to compute topography of the surface as shown at box 322. Optionally, as shown at box 324, a measurement from a force sensor can be obtained. At box 326, a stiffness map can be calculated based on the combination of computed topography and recorded forces from the force sensor. The calculated maps and other data can be saved, as shown at box 328, in data storage and/or can be transmitted for inclusion in a patient medical record.

With reference to FIG. 12B, another process for obtaining and analyzing an image from the palpation device is illustrated. This mode of operation is referred to as a Screening or Scout Mode. Initially, the user places the sensor on the tissue of interest and applies pressure to the sensor as described above in connection with the process illustrated in FIG. 12A. At box 410, the user is prompted to move or displace the lens to collect sequential frames (which can be adjusted to be calculated in near real-time). As the user moves the device, sequential images are recorded at box 412. As discussed above in connection with the process of FIG. 12A, the recorded images can be analyzed by boundary detection. In addition, the topography of the lens and/or a stiffness of the underlying tissue can be calculated. At box 414, shape recognition and classification algorithms can be applied to the obtained images. For example, the analysis of sequential frames can be executed with an optical flow algorithm, described by Liu and can be implemented in Matlab. See C. Liu, "Beyond Pixels: Exploring New Representations and Applications for Motion Analysis," Massachusetts Institute of Technology, 2009. This algorithm performs cross-correlation pixels of similar intensities between frames and tracks the motion of the lesion within the frame during palpation. By tracking the motion of the lesion as well as its size and shape in each frame, the present invention is able to quantify the boundary of the region during motion and determine the presence of a lesion in a single frame.

A further function of the software may be to concatenate adjacent frames to produce a larger map, or panorama, of the breast. In the event that a suspected lesion is detected as shown at box 416, the software may prompt the user to repeat the scan in Spot Mode, in the manner described in connection with FIG. 12A, so as to obtain a more accurate assessment of the specific region. If no suspected lesions are identified, the user can be instructed to stop using the device. For example, the device can be configured to provide an end of use indication, such as visual or audio feedback, indicating that the test is completed.

While several embodiments of the palpation device, image device, monitoring system, and image capture and processing methods are shown in the accompanying figures and described hereinabove in detail, other embodiments will be apparent to, and readily made by, those skilled in the art without departing from the scope and spirit of the invention. For example, it is to be understood that this disclosure contemplates that, to the extent possible, one or more features of any embodiment can be combined with one or more features of any other embodiment. Accordingly, the foregoing description is intended to be illustrative rather than restrictive.

What is claimed is:

1. A palpation device for palpation of tissue of a patient for identification of an object embedded therein by visual inspection through the palpation device, the device comprising:
   a frame formed from a substantially rigid material and comprising an opening;
   a tonometric lens extending through the opening of the frame, the tonometric lens comprising a surface configured to be applied to the tissue of the patient to at least partially impinge the tissue, and configured to be looked through to view a topography of the surface of the tonometric lens when the lens is applied to the tissue to identify one or more objects embedded in the tissue of the patient based, at least in part, on the view of the topography of the surface of the tonometric lens, the lens comprising a body having a reflective coating on an outer surface thereof; and
   a radiation source positioned to illuminate the reflective coating such that the topography of the surface of the tonometric lens can be observed,
   wherein the body comprises a body material that is as stiff or stiffer than the tissue of the patient and less stiff than the embedded object.

2. The device of claim 1, further comprising a force sensor configured to measure force applied by the lens to the tissue.

3. The device of claim 2, wherein the force sensor is mounted between the lens and frame, and comprises one or more of a strain gauge and a piezoelectric transducer.

4. The device of claim 1, wherein the radiation source emits visible light.

5. The device of claim 1, wherein the body of the lens comprises a curved profile.

6. The device of claim 1, wherein the body material comprises a material having a Shore hardness of between 00-16 and 00-32.

7. The device of claim 1, wherein the reflective coating comprises fine particles comprising one or more of mica, iron oxide, titanium dioxide, silver, aluminum, gold, platinum, chrome, nickel, Inconel, titanium nitride, zinc oxide, copper, zinc, stearic acid, titanium dioxide, clay, calcium carbonate, silica, and talc.

8. The device of claim 1, wherein the radiation source comprises a first radiation source emitting radiation having a first wavelength and a second radiation source emitting radiation having a second wavelength, the first wavelength being different from the second wavelength.

9. A system for palpating a tissue of a patient to identify an object embedded therein, the system comprising:
   a palpation device for palpation of the tissue of the patient for identification of the object embedded therein by visual inspection through the palpation device, the device comprising:
      a frame formed from a substantially rigid material and comprising an opening, and
      a tonometric lens extending through the opening of the frame, the tonometric lens comprising a surface configured to be applied to the tissue of the patient to at least partially impinge the tissue, and configured to be looked through to view a topography of the surface of the tonometric lens when the lens is applied to the tissue to identify one or more objects embedded in the tissue of the patient based, at least in part, on the view of the topography of the surface of the tonometric lens, the lens comprising a body having a reflective coating on an outer surface thereof; and
   an image device connected to or in communication with the palpation device, the image device comprising:
      at least one optical sensor positioned to obtain an image of the topography of the surface of the tonometric lens, and
      a processor configured to:
         receive at least one image from the optical sensor,
         process the image to identify an area of interest in the image, and
         provide feedback regarding the image and/or the area of interest,
      wherein the body of the lens comprises a body material that is as stiff or stiffer than the tissue of the patient and less stiff than the embedded object.

10. The system of claim 9, wherein the optical sensor comprises a video camera.

11. The system of claim 9, wherein the coating comprises fine particles comprising one or more of mica, iron oxide, titanium dioxide, silver, aluminum, gold, platinum, chrome, nickel, Inconel, titanium nitride, zinc oxide, copper, zinc, stearic acid, titanium dioxide, clay, calcium carbonate, silica, and talc.

12. The system of claim 9, wherein the palpation device further comprises a force sensor configured to determine a force that the palpation device applies to the tissue of interest.

13. The system of claim 12, wherein processing the image comprises identifying a displacement of the lens at the area of interest, and calculating a stiffness for the area of interest based, at least in part, on the calculated displacement and the force.

14. The system of claim 9, further comprising a location identification sensor for identifying a location of the palpation device on the body of the patient.

15. The system of claim 9, further comprising a visual display, and wherein providing feedback comprises providing the image on the visual display.

16. A method for palpation of tissue of a patient for identification of an object embedded therein by visual inspection through a palpation device, the method comprising:
   applying a surface of a tonometric lens of the palpation device to the tissue of the patient to at least partially impinge the tissue;
   looking through the tonometric lens to view a topography of the surface of the tonometric lens once the lens is applied to the tissue; and
   identifying one or more objects embedded in the tissue of the patient based, at least in part, on the view of the topography of the surface of the tonometric lens.

17. The method of claim 16, wherein the tonometric lens comprises a body and a reflective coating on at least a portion of the surface of the tonometric lens.

18. The method of claim 17, wherein the body of the lens comprises a body material that is as stiff or stiffer than the tissue and less stiff than the one or more embedded objects.

19. The method of claim 17, further comprising directing light through the tonometric lens to illuminate an inner side of the reflective coating of the lens so that viewing of the topography of the tonometric lens is improved.

20. The method of claim 17, wherein the reflective coating comprises fine particles comprising one or more of mica, iron oxide, titanium dioxide, silver, aluminum, gold, platinum, chrome, nickel, Inconel, titanium nitride, zinc oxide, copper, zinc, stearic acid, titanium dioxide, clay, calcium carbonate, silica, and talc.

21. The method of claim 16, further comprising determining a force that the surface of the tonometric lens of the palpation device applies to the tissue.

22. The method of claim 21, further comprising calculating a stiffness for a portion of the tissue, the stiffness being based on a displacement of the tissue and the force.

23. The method of claim 16, further comprising identifying a stiffness at multiple locations on the topography of the tissue and creating a map illustrating differences in the stiffness based on the identified stiffness at multiple locations.

24. The method of claim 16, wherein the tonometric lens comprises an optically clear material so that the surface of the lens can be viewed through the tonometric lens.

25. The method of claim 16, wherein the tissue of the patient comprises breast tissue and the object comprises a lesion embedded in the breast tissue.

26. The method of claim 16, wherein the surface of the tonometric lens comprises a curved profile configured to contact the tissue of the patient.

27. The method of claim 16, wherein the palpation device comprises:
   a frame formed from a substantially rigid material and comprising an opening;
   the tonometric lens extending through the opening of the frame, the lens comprising a body and a reflective coating on a surface of the body; and
   a radiation source mounted to the frame positioned to illuminate an inner surface of the reflective coating through the tonometric lens, such that a topography of the coating can be more clearly observed, and
   wherein the body comprises a body material that is as stiff or stiffer than the tissue of interest and less stiff than the embedded object.

28. The method of claim 27, wherein the radiation source emits visible light.

29. The method of claim 27, wherein the body material comprises a material having a Shore hardness of between 00-16 and 00-32.

* * * * *